US 008858971B2

(12) United States Patent
Rao

(10) Patent No.: US 8,858,971 B2
(45) Date of Patent: Oct. 14, 2014

(54) EPIDERMAL COOLING

(71) Applicant: Exert Co., Wilmington, DE (US)

(72) Inventor: Arvind M. Rao, Rochester, NY (US)

(73) Assignee: Exert Co., Wilmington, DE (US)

( * ) Notice: Subject to any disclaimer, the term of this patent is extended or adjusted under 35 U.S.C. 154(b) by 0 days.

(21) Appl. No.: 13/922,368

(22) Filed: Jun. 20, 2013

(65) Prior Publication Data

US 2014/0050672 A1 Feb. 20, 2014

Related U.S. Application Data

(62) Division of application No. 13/587,445, filed on Aug. 16, 2012.

(51) Int. Cl.

| *A61K 8/02* | (2006.01) |
| *A61K 9/12* | (2006.01) |
| *A61K 9/00* | (2006.01) |
| *A61K 8/00* | (2006.01) |
| *A01N 25/00* | (2006.01) |
| *C07C 53/00* | (2006.01) |
| *C07F 7/08* | (2006.01) |
| *A61K 36/889* | (2006.01) |
| *A61F 7/00* | (2006.01) |
| *A61K 31/23* | (2006.01) |
| *A61K 36/185* | (2006.01) |
| *A61F 7/02* | (2006.01) |

(52) U.S. Cl.
CPC ............... *A61K 31/23* (2013.01); *A61K 36/889* (2013.01); *A61F 7/0085* (2013.01); *A61F 2007/0292* (2013.01); *A61K 36/185* (2013.01); *Y10S 514/919* (2013.01)
USPC ............... 424/401; 424/45; 424/47; 424/59; 424/70.19; 424/404; 424/405; 514/919; 554/1; 556/445

(58) Field of Classification Search
None
See application file for complete search history.

(56) References Cited

U.S. PATENT DOCUMENTS

| 6,153,209 A | 11/2000 | Vega et al. |
| 6,648,904 B2 | 11/2003 | Altshuler et al. |
| 6,699,266 B2 | 3/2004 | Lachenbruch et al. |
| 6,815,486 B2 | 11/2004 | Bhagwagar et al. |
| 7,255,870 B2 | 8/2007 | Lennon et al. |
| 7,399,919 B2 | 7/2008 | McCutcheon et al. |
| 8,039,011 B2 | 10/2011 | Flugge-Berendes et al. |
| 2001/0003565 A1 | 6/2001 | Mcosker et al. |
| 2002/0164473 A1 | 11/2002 | Buckley |
| 2005/0053632 A1* | 3/2005 | Schafer et al. ................ 424/401 |
| 2005/0169878 A1* | 8/2005 | Elder et al. ................ 424/70.122 |
| 2006/0135911 A1 | 6/2006 | Mittur |
| 2008/0199421 A1 | 8/2008 | Lorant |
| 2009/0110656 A1 | 4/2009 | Lemke et al. |
| 2009/0157153 A1 | 6/2009 | Lemke et al. |
| 2009/0324713 A1* | 12/2009 | Ulman et al. ................ 424/464 |
| 2011/0027331 A1 | 2/2011 | Hobot |

OTHER PUBLICATIONS

USPTO Office Action dated May 20, 2013 in co-pending U.S. Appl. No. 13/587,445 (68 pages).
Handbook of Pharmaceutical Excipients (Oct. 13, 1988) Entry for Talc: pp. 321-324 (5 pages, incl. cover).
Gravante et al.: Reconstructive Surgery: Ann R. Coll Surg Engl 92: 118-123, dated 2010.
Khodakov et al.: J. Phys Chem B 2001: 105, 9805-9811.
PubChem CID 8181 (http://pubchem.ncbi.nim.nih.gov/summary.cgi?cid=8181&loc=ec_rcs)—methyl palmitate; downloaded May 8, 2013 (4 pages).
Sample Google search string for methyl palmitate properties; downloaded May 8, 2013 (2 pages).
PubChem CID 8201 (http://pubchem.ncbi.nim.nih.gov/summary.cgi?cid=8201&loc=ec_rcs)—methyl stearate; downloaded May 8, 2013 (5 pages).
Geology.com web archive dated Jun. 14, 2012 (4 pages) (http://web.archive.org/web/20120614215422/http://geology.com/minerals/talc.shtml); downloaded May 10, 2013.
Co-pending U.S. Appl. No. 13/412,919, filed Mar. 6, 2012 (16 pages).

* cited by examiner

*Primary Examiner* — Jeffrey T Palenick
(74) *Attorney, Agent, or Firm* — McCarter & English, LLP

(57) ABSTRACT

In one aspect, an epidermal coolant dispensable by an aerosol container includes a phase change material that changes phase between about 28-degrees and 40-degrees Celsius. The coolant also includes a solvent in which the phase change material is dissolved and a surfactant. The coolant may further include a propellant to express the product from the aerosol container. In another aspect, an epidermal coolant includes a porous material and a phase change material retained in the porous material. The phase change material has a melting point between about 0-degrees Celsius and about 65-degrees Celsius and is retained in the porous material when the phase change material is in either the solid or liquid phase.

18 Claims, No Drawings

EPIDERMAL COOLING

BACKGROUND OF THE INVENTION

1. Field of the Invention

This invention relates to cooling. More specifically, the invention relates to a formulation including a phase change material provided for intimate contact with a user's epidermis to cool the epidermis in response to increased heat.

2. Description of Related Art

Several products are commercially available that are intended to combat uncomfortable sensations experienced in response to bodily heating. For example, patches containing menthol or some other similar substance are provided for application by a user to the user's epidermis, to impart on the user a cooling sensation. Such patches are marketed for application to the forehead when running a fever or to an injury site, such as a sprain. Other sources of increased epidermal temperature also are known, for example, due to exercise, drug side effects or hormonal imbalances, including as a result of menopause.

Menthol-based and similar conventional cooling solutions, however, are single use and do not actually cool the body. Menthol creates the illusion of cooling because it activates TRPM8, a protein in the body that perceives cold. Once the menthol dissipates, it is gone though. Moreover, because menthol is only "tricking" the body into feeling cool, it does not actually create any epidermal temperature change.

Thus, there is a need for reusable or reversible cooling relief that a user can apply to a desired site on the epidermis.

There is a further need for fast-acting cooling relief with continued efficacy over an extended period of time.

There also is a need for cooling relief that lowers the temperature of the epidermis.

There is also a need for cooling relief that is activated by increasing skin temperature and can be reactivated every time the skin temperature increases over a 24-hour period without additional application.

BRIEF SUMMARY OF THE INVENTION

This invention addresses these needs by providing improvements in epidermal cooling.

In one aspect of the invention, an epidermal coolant dispensable by an aerosol container includes a phase change material that changes phase between about 28-degrees and 40-degrees Celsius. The coolant also includes a solvent in which the phase change material is dissolved and a surfactant. The coolant may further include a propellant to express the product from the aerosol container.

In another aspect of the invention, an epidermal coolant includes a porous material and a phase change material retained in the porous material. The phase change material has a melting point between about 0-degrees Celsius and about 65-degrees Celsius and is retained in the porous material when the phase change material is in either the solid or liquid phase.

In a further aspect of the invention, the epidermal coolants described above may be formulated with other skin care additives such as perfumes, sunscreens and antimicrobials.

An understanding of these and other aspects, features, and benefits of the invention may be had with reference to the following disclosure, in which preferred embodiments of the invention are described.

DETAILED DESCRIPTION OF THE INVENTION

As noted above, the invention generally relates to epidermal cooling and more specifically to cooling compositions that can be applied to a user's epidermis in a conventional form and using conventional methods.

In one embodiment of the invention, an epidermal cooling composition or body coolant is formed as a composite phase change material that includes a porous material and a phase change material retained in the pores of the porous material. The porous material may be a mesoporous filler, with pores ranging in size from about 2 to about 50 nanometers. The phase change material is preferably any material that can readily change back-and-forth between two states, e.g., solid and liquid, with applied temperatures. The phase change material is retained in the pores whether the phase change material is in the solid state or the liquid state and thus, under changing ambient conditions, is free to melt and re-solidify without separating from the filler. Thus, when applied to a user's skin, for example, the phase change material will melt when the user's body temperature rises above the melting point and the resulting endothermic reaction will cool the user's skin. When the user's body temperature returns to normal, i.e., below the melting point of the phase change material, the material will return to its solid form, ready to melt again when the user warms.

In preferred embodiments of the invention, the phase change material has a melting point of between about 0-degrees Celsius and about 65-degrees Celsius, and more preferably between about 28-degrees Celsius and about 40-degrees Celsius. Phase change materials of this type include, but are not limited to, metal salts, hydrated metal salts, waxes, n-alkanes or paraffin, fatty acids, fatty acid esters, monoglycerides, diglycerides, triglycerides, and polyethylene glycol. More specifically, the phase change material may include coconut oil (cocos nucifera, refined bleached deodorized, 24-degrees Celsius melting point), methyl palmitate (methyl ester of palmitic Acid, 32-degrees Celsius melting point), shea butter oil (butyrospermum parkii, 32-degrees Celsius melting point), palm kernel oil (refined bleached deodorized, 32-degrees Celsius melting point), methyl stearate (38-degrees Celsius melting point), an 40/60% blend of methyl stearate and ethyl stearate (32-degrees Celsius melting point), retinyl palmitate (28-degrees Celsius melting point), erucic acid (33.8-degrees Celsius melting point), decanoic acid (31.6-degrees Celsius melting point), and undecylic (or undecanoic) acid (28.6-degrees Celsius melting point), cetyl palmitate (hexadecyl ester of palmitic Acid, 53-degrees Celsius melting point) and beeswax (62-degrees Celsius melting point).

As noted above, in presently preferred embodiments, the filler is a mesoporous filler. Non-limiting examples of such fillers include diatomaceous earth, kaolin, calcined kaolin (dehydrated), vermiculite, fumed silica, Fuller's earth, aerogels, expanded graphite, carbon nanotubes, and zeolites.

In a simple example, the phase change material is melted and mixed with the mesoporous filler, so the mesoporous filler adsorbs the phase change material into its pores. Once adsorbed, the phase change material will be retained there in both its solid and liquid form. More detailed example formulations and methods of creating those formulations will be described below.

A formulation consisting of just a phase change material retained in a porous filler may be used in certain body cooling applications. However, in most applications additional materials will be needed. For example, preservatives or antioxidants, such as butylated hydroxyl-toluene and citric acid may be included in the formulation. Moreover, moisture-absorbing agents may also be included, such as talc, maranta arundinacea (arrowroot) powder, and cornstarch powder. Depending upon the application, anticaking agents, like cyclomethicone or a silicone elastomer blend including cyclomethicone and dimethicone crosspolymer, may also be used.

Compositions made in accordance with this disclosure generally include between about 12% and about 50% of the phase change material. More preferably, the phase change material is present in the composition in an amount from about 25% to about 40%.

The inventor has experimented with a number of delivery modalities for phase change compositions like those described above. As will be appreciated, some of the applications utilize a mesoporous filler to contain the phase change material as in the preparation of powders, body sticks, creams or lotions, while others required the phase change material to be combined directly with a favorable solvent as in the preparation of transparent gels, atomized or aerosol sprays, or wet wipes.

EXAMPLE 1 details the first combination of the phase change material with the mesoporous filler. 35 g of refined bleached and deodorized (RBD) coconut oil (a mixture of medium chain triglycerides with a melting point of 24-degrees Celsius commercially available from Interstate Chemical of Hermitage, Pa.) was melted in a heated mixer at 60 RPM using a hot water bath with a temperature of 50-60-degrees Celsius. Once melted, 65 g of diatomaceous earth (a mesoporous filler from Interstate Chemical of Hermitage, Pa.) was added and combined for 3 min at 80 RPM. The mixing bowl was then transferred to a freezer at temperature of 0-degrees Celsius for 10 min to harden the mixture. The hardened mixture was then ground into a fine powder in a coffee grinder, resulting in a fine powder with a particle size range between about 100 to 500 microns.

EXAMPLE 2 provides epidermal cooling using the aforementioned phase change materials in the form of a powder commonly administered to the skin by hand, makeup brush or dry roll-on. 25 g of methyl palmitate (methyl ester of palmitic acid phase change material with a melting point of 32-degrees Celsius from Acros Organics of Geel, Belgium) were melted in a heated mixer at 80 RPM using a hot water bath with a temperature of 70-degrees Celsius. Once melted, 25 g of calcined kaolin (Kamin 2000C from KaMin LLC of Macon, Ga.) was added and blended at 80 RPM for 5 minutes. With the bath temperature reduced slowly to 50 to 60-degrees Celsius, 13 g of talc, 25 g of arrowroot (from Interstate Chemical of Hermitage, Pa.), 5 g of mica (cosmetic grade mica with particle size less than 15 microns from Making Cosmetics.com of Renton, Wash.), 5 g of baking soda and 2 g of cyclomethicone and dimethicone crosspolymer silicone elastomer blend (EXP 578 from Interstate Chemical of Hermitage, Pa.) were added. The mixing bowl was then removed from heat and covered. The mixer speed was then increased to 120 RPM and allowed to cool slowly below the melting point of the methyl palmitate. The high speed mixing produces a fine powder. EXAMPLES 4 and 5 were prepared similarly.

EXAMPLE 3 describes the use of the aforementioned powder in an aerosol spray system. The methyl palmitate and powder ingredients were prepared in a similar fashion as in EXAMPLE 2. To this, 5 g of ethyl alcohol and 5 g of cyclomethicone (from Interstate Chemical of Hermitage, Pa.) was combined. The resultant mixture was fed into an aerosol can and charged with 73.3 g of n-butane. EXAMPLES 6 and 7 were prepared similarly.

EXAMPLE 8 provides epidermal cooling using the aforementioned phase change materials in the form of a body stick commonly administered to the skin similar to a deodorant stick. 20 g of shea butter oil and 30 g of coconut oil were melted in a heated mixer at 80 RPM using a hot water bath with a temperature of 60-degrees Celsius. Once melted, 30 g of calcined kaolin was added and blended at 80 RPM for 5 minutes. After 3 minutes of mixing, the remaining ingredients were added and mixed for an additional 5 minutes at 80 RPM to produce a homogeneous viscous paste. The warm paste was immediately poured into a twist up deodorant tube and allowed to solidify as it cooled. EXAMPLES 9 through 12 were prepared similarly.

The Example formulations described above are shown in the following tables, in which the Example number at the top of each column correlates to the Example described above.

TABLE 1.1 dry powder formulations

| EXAMPLES | 1 | 2 | 3 | 4 | 5 |
|---|---|---|---|---|---|
| Product Form | Powder, non-dusting | Powder, non-dusting | Aerosol spray powder | Powder, non-dusting | Powder, non-dusting |
| Diatomaceous earth powder | 65 | | | | |
| Kaolin, calcined | | 25 | 5 | 25 | 25 |
| Talc | | 13 | 3 | | |
| Silicone Elastomer blend | | 2 | 0.2 | 1 | 1 |
| Coconut oil, RBD | 35 | | | 10 | |
| Methyl Palmitate | | 25 | 5 | 15 | 25 |
| Sodium Bicarbonate (Baking soda) | | 5 | | 13 | 15 |
| Maranta arundinacea (arrowroot) powder | | 25 | 3 | 18 | 5 |
| Mica | | 5 | 0.5 | 2.9 | 2.9 |
| Ethyl Alcohol SDA 40B 200 | | | 5 | | |
| Cyclomethicone | | | 5 | | |
| n-Butane | | | 73.3 | | |
| BHT | | | | 0.1 | 0.1 |
| Cornstarch powder | | | | 5 | 14 |
| Citric acid | | | | 10 | 12 |

TABLE 1.2 powder aerosol formulations

| Product Form | 6 | 7 |
|---|---|---|
| | Aerosol spray powder | Aerosol spray powder |
| Kaolin, calcined | 12.5 | 12.5 |
| Silicone Elastomer blend | 0.5 | 0.5 |
| Methyl Palmitate | 12.5 | 12.5 |
| Sodium Bicarbonate (Baking soda) | 7.5 | 7.5 |
| Maranta arundinacea (arrowroot) powder | 2.5 | 2.5 |
| Mica | 1.45 | 1.45 |
| HDMS PSF-0.65cSt Silicone fluid | 50 | 44 |
| BHT | 0.05 | 0.05 |
| Cornstarch powder | 7 | 7 |
| Citric acid | 6 | 6 |
| Shea butter oil with perfume | | 1 |
| Isopropyl Myristate | | 5 |

TABLE 1.3 body stick formulations

| Product Form | 8 | 9 | 10 | 11 | 12 |
|---|---|---|---|---|---|
| | Body stick | Body stick | Body stick | Body stick | Body stick |
| Kaolin, calcined | 30 | 50 | 40 | 30 | 30 |
| Talc | | | | | 5 |
| Methyl palmitate | | | | 40 | 20 |
| Sodium Bicarbonate (Baking soda) | | | | | |
| Maranta arundinacea (arrowroot) powder | 10 | | 10 | 20 | 20 |
| Butyrospermum parkii, Shea Butter oil | 20 | | 5 | 3 | 10 |
| Coconut oil, RBD | 30 | 50 | 10 | 4 | 10 |
| Palm kernel oil, RBD | | | 30 | | |
| Beeswax | 5 | | | | |
| Mica | 4.9 | | 4.9 | 2.9 | 4.9 |
| BHT | 0.1 | | 0.1 | 0.1 | 0.1 |

Efficacy of several of the foregoing examples was tested against comparative examples on a test subject, and the results of those tests are provided in the following tables 2.1-2.3. In the tables, NT means no treatment. In tests marked "NT," the skin was cleaned and dried prior to testing, but nothing was applied to the skin. Also in the tables, CA1 is the commercially available men's Speed Stick Fresh Antiperspirant Deodorant stick by Mennen with 16% aluminum zirconium tetrachlorohydrex glycine as the active ingredient and CA2 is the commercially available Gillette Clinical Strength Advanced Solid Antiperspirant by Proctor & Gamble with 20% aluminum zirconium trichlorohydrex glycine as the active ingredient.

Tables 2.1-2.3 also reference a separation/stability procedure test in which the formulations were tested to determine whether the phase change material would separate from the porous material. Obviously, this would be undesirable because separation once applied to the body would result in lessened effectiveness or even ineffectiveness in some instances. Moreover, separation could result in staining of clothing or the like. The separation/stability procedure was accomplished by placing the formulation in a thin line (approximately 5 cm long, about 0.5 cm tall, and about 0.5 cm wide) at the bottom of a stainless steel vessel. The vessel was then placed above, but not in contact with, a beaker containing boiling water. The time to separation was then noted when the molten phase change material (a clear liquid) formed a pool outside the perimeter of the lines. In the absence of a change in appearance, the test was terminated after 20 minutes. A formulation that made it a full 20 minutes is a very stable composition, given the very harsh test conditions.

The "performance test" referenced in tables 2.1-2.3 is a measurement of the amount of sweat transferred from the subject's armpit to his t-shirt after a 30-minute exercise period. "Application ease" refers a subjective observation of how easily the body stick formulations were applied. "Clumping" means that application resulted in clumping of the formulation, "smooth-thick" means that an even layer of formulation went on to the skin, having a thickness of approximately 0.5 to 1 mm, and "smooth-thin" means that an even layer of the formulation readily went on to the skin having a thickness of less than approximately 0.5 mm.

The "sweat area" is a measurement (in square centimeters) of sweat transferred from subject's armpit to his t-shirt (medium-weight cotton) after approximately 30-minutes of moderate cardiovascular exercise. A subjective assessment of whether body odor was present at the application site after the 30-minute exercise period, as well as indications of whether the subject's shirt was stained after exercise (i.e., to determine staining from the composition) and whether the wearer experienced any skin irritation also are included in Tables 2.1-2.3. Those tables are provided here:

TABLE 2.1 test results

| | EXAMPLE 2 | Comparative CA1 | EXAMPLE 4 | Comparative CA1 | EXAMPLE 5 | Comparative CA1 |
|---|---|---|---|---|---|---|
| Product Form | Powder, non-dusting | Antiperspirant stick | Powder, non-dusting | Antiperspirant stick | Powder, non-dusting | Antiperspirant stick |
| Separation/Separation test | 20 min | Not Tested | 20 min | Not Tested | 20 min | Not Tested |
| Test subject details | 42 year old male, asian, history of mild hyperhidrosis | 42 year old male, asian, history of mild hyperhidrosis | 42 year old male, asian, history of mild hyperhidrosis | 42 year old male, asian, history of mild hyperhidrosis | 42 year old male, asian, history of mild hyperhidrosis | 42 year old male, asian, history of mild hyperhidrosis |
| Application location | Left armpit | Right armpit | Left armpit | Right armpit | Left armpit | Right armpit |
| Application amount | 2.1 g (1 teaspoon) | 2 swipes | 2.1 g (1 teaspoon) | 2 swipes | 2.1 g (1 teaspoon) | 2 swipes |
| Ambient Conditions | Outdoors, 75° F., 50% RH, bright sunshine | Outdoors, 75° F., 50% RH, bright sunshine | Indoors, 80° F. | Indoors, 80° F. | Indoors, 80° F. | Indoors, 80° F. |

TABLE 2.1-continued test results

|  | EXAMPLE 2 | Comparative CA1 | EXAMPLE 4 | Comparative CA1 | EXAMPLE 5 | Comparative CA1 |
|---|---|---|---|---|---|---|
| Sweat Area (cm2) | 24 | 201 | 35 | 223 | 28 | 198 |
| Odor | No | Body odor | No | Body odor | No | Body odor |
| Staining/transfer to clothing | No | No | No | No | No | No |
| Skin irritation | No | No | No | No | No | No |

TABLE 2.2 test results

|  | EXAMPLE 8 | Comparative CA1 | EXAMPLE 9 | EXAMPLE 10 | Comparative CA1 |
|---|---|---|---|---|---|
| Product Form | Body stick | Antiperspirant stick | Body stick | Body stick | Antiperspirant stick |
| Separation/Separation test | 20 min | Not tested | 20 min | 20 min | Not Tested |
| Test subject details | 42 year old male, asian, history of mild hyperhidrosis | 42 year old male, asian, history of mild hyperhidrosis |  | 42 year old male, asian, history of mild hyperhidrosis | 42 year old male, asian, history of mild hyperhidrosis |
| Application location | Left armpit | Right armpit |  | Left armpit | Right armpit |
| Application amount | 2 swipes | 2 swipes |  | 2 swipes | 2 swipes |
| Ambient Conditions | Outdoors, 75° F., 50% RH, sunshine | Outdoors, 75° F., 50% RH, sunshine |  | Outdoors, 55° F., 40% RH, cloudy | Outdoors, 55° F., 40% RH, cloudy |
| Sweat Area (cm2) | 195 | 203 |  | 172 | 188 |
| Odor | Body odor | Body odor |  | No | No |
| Staining/transfer to clothing | No | No |  | No | No |
| Skin irritation | No | No |  | No | No |
| Application ease | Smooth-thick | Smooth-thin |  | Smooth-thin | Smooth-thin |

TABLE 2.3 test results

|  | EXAMPLE 11 | EXAMPLE 12 | Comparative CA1 |
|---|---|---|---|
| Product Form | Body stick | Body stick | Antiperspirant stick |
| Separation/Separation test | 6 min | 20 min | Not Tested |
| Test subject details |  | 42 year old male, asian, history of mild hyperhidrosis | 42 year old male, asian, history of mild hyperhidrosis |
| Application location |  | Left armpit | Right armpit |
| Application amount |  | 2 swipes | 2 swipes |
| Ambient Conditions |  | Outdoors, 75° F., 50% RH, sunshine | Outdoors, 75° F., 50% RH, sunshine |
| Sweat Area (cm2) |  | 80 | 186 |
| Odor |  | No | Antiperspirant scent |
| Staining/transfer to clothing |  | Yes | No |
| Skin irritation |  | No | No |
| Application ease | Smooth-thin | Smooth-thin | Smooth-thin |

Thus, as is readily apparent from the tables, several of the formulations are stable over a 30-minute exercise period, and outperformed the comparative, commercially available compositions in both stopping odor and reducing sweat. The inventor believes that this improved performance is a direct result of the phase change material's cooling effect.

A thermal conductivity agent in the form of a fine powder (particle size less than 25 microns) or nanoparticle may also be included with any of the phase change materials provided above. Such materials have a thermal conductivity greater than about 7 W/mK. The inventor has experimented with additives including beryllium oxide (having a thermal conductivity of about 272 W/mK), quartz (12 W/mK), natural diamond (2200 W/mK), talc (10.7 W/mK), titanium dioxide (8.4 W/mK), magnesium oxide (30-48 W/mK), graphene (4500-5300 W/mK), carbon nanotubes (3100-3500 W/mK), silver (430 W/mK), aluminum oxide (25-36 W/mK), and bismuth (7.9 W/mK). Other thermal conductivity additives also may be used without departing from the spirit and scope of the invention.

The inventor has found that the combination of the phase change material with the thermal conductivity agent leads to a greater cooling effect for the wearer, and more quickly. Whereas the phase change material will take time to melt upon application to a wearer's skin, or when the wearer's skin rises to a temperature necessary to melt the phase change material, the thermal conductivity agent immediately begins to conduct heat away from the user's skin. This conducted heat will immediately begin to cool the user's skin. Moreover, because the thermal conductivity additive is dispersed among the phase change material, the phase change material is more readily heated up, resulting in a quicker melting of the phase change material. As the material melts, the accompanying endothermic reaction absorbs heat, creating a temperature decrease around the phase change material, further cooling the user's skin situated proximate the composition. The thermal conductivity agent further conducts this cooling to the skin.

To achieve maximum cooling, formulations according to the invention are intended to be placed in close proximity to, or in intimate contact with, the user's epidermis. Accordingly, the formulations discussed above are applicable directly on the skin, e.g., as a cooling powder or as a deodorant stick. Other formulations also are contemplated, such as gels, wet wipes, creams, pastes, or lotions. In still other embodiments, the inventive formulations may be provided in a peel or they may be provided on a substrate, for example, in the form of a mask, tape, or patch.

An additional contemplated formulation is a spray-on formulation usable with aerosol dispensers. The inventor has experimented with a number of formulations that are intended to be used in this manner. In one formulation, a composition such as that described above, in which a phase change material is retained in the pores of a filler, was finely ground into a powder that was then suspended in low viscosity silicone oil. The particle sizes of the powders were too large to spray properly, so they were further filtered, using cheesecloth. The filtered compositions would spray better, but were still not fine enough to provide reproducible spraying.

Faced with the mediocre results of the suspended powders, the inventor instead devised a liquid-only system. In a basic form, the liquid-only system includes only a phase change material, a solvent, and a surfactant or film former. Any of the above-listed phase change materials may be used, depending upon the application, but the inventor has found that methyl palmitate performs well and is readily available.

The solvent is chosen to effectively dissolve the phase change material. The solvent preferably also flashes or evaporates upon contact with the user's skin. The solvent should preferably evaporate cleanly when it comes in contact with warm skin, leave no residue, be non-irritating and have a clean environmental profile (low or, more preferably no, volatile organic compounds (VOCs)). Ethanol, perfumer's ethanol, and low viscosity silicone fluid are non-limiting examples of solvents that may be used in formulations of the invention. In some applications, however, ethanol may not be preferred, as it can be irritating to the skin in concentrations greater than about 40%). One example of a low viscosity silicone fluid used by the inventor in some formulations is hexamethyldisiloxane (PFS-0.65 cSt from Clearco Products Co., Inc., Bensalem, Pa.).

The surfactant/film former aids in making the phase change material more soluble in the solvent, namely, because it includes chemical groups that are soluble in both the phase change material and the solvent. Moreover, the surfactant inhibits the migration of the phase change material, both along the skin, e.g., when the skin gets wet, and through the skin, e.g., via absorption. In some embodiments, the surfactant forms a smooth, silky film on the user's epidermis that holds the phase change material in place.

The surfactant may include a high molecular weight silicone. Materials tested by the inventor include a blend of cyclopentasiloxane and dimethiconol (DC1501 by Dow Corning, TSIL 1501 by Trico Products, CDM15 by Access Chemicals), a silicone elastomer blend of cyclomethicone and dimethicone Crosspolymer (DC9045 by Dow Corning, EXP578 by Trico Products) and propylene glycol USP pharma grade. Formulations using perfumer's alcohol (SDA40B 200) may already contain propylene glycol.

Formulations according to this disclosure were prepared and were found to be useful in pump sprayers and in bag-on-valve aerosol systems. In certain applications, a propellant such as butane or propane is necessarily mixed with the formulation so the formulation can be expelled from the aerosol container. Other aerosol dispensing systems do not need a propellant.

The inventor has prepared a number of cooling formulations for use with aerosol dispensers (including propellant delivered, bag-on-valve or pump atomized sprayer). The formulations are set forth in the following tables 3.1-3.3. These tables also include results of shelf life tests conducted at room temperature and at low temperature, in which the solubility of the phase change material was observed.

EXAMPLE 13 was prepared by first melting the methyl palmitate. In a separate container the surfactants (silicone, silicone elastomer blend and hexamethyldisiloxane) were combined. The methyl palmitate was then added to the mixture and combined until a water clear solution was obtained. EXAMPLES 14 through 26 were prepared similarly.

TABLE 3.1 aerosol compositions

| Example | 13 | 14 | 15 | 16 |
|---|---|---|---|---|
| Intended Form/Background/Detail | Aerosol/Spray concentrate | Aerosol/Spray concentrate | Aerosol/Spray concentrate | Aerosol/Spray concentrate |
| Methyl Palmitate | 50 | 40 | 40 | 40 |
| TSIL 1501 Silicone | 5 | 5 | 7.5 | 2.5 |
| Silicone Elastomer blend | 3 | 5 | 2.5 | 7.5 |
| Hexamethyldisiloxane | 42 | 50 | 5 | 50 |
| Batch Size (g) | 100 g | 100 g | 100 g | 100 g |
| Processing Observations | Water clear solution | Water clear solution | Water clear solution | Water clear solution |
| Stability-12 hr-Room temp | Complete separation, MEP crystals at bottom of jar | No separation-slight haze | No separation-clear | No separation |
| Stability-24 hr-Room temp | | No separation | No separation-slight haze | No separation |
| Stability-48 hr-Room temp | | No separation | Complete separation, MEP crystals at bottom of jar | No separation |
| Testing | | | Jun. 19, 2012-Sample sent to Christine Hosler, Aptar for BOV development | |
| Pump sprayer | | Tested-Coarse particle size spray achieved | | Tested-successful fine particle size spray achieved |

TABLE 3.1-continued aerosol compositions

| Example | 13 | 14 | 15 | 16 |
|---|---|---|---|---|
| Aerosol | Tested-Coarse particle size spray achieved | | Not tested | |
| BOV Aerosol | | Not tested | Tested-successful fine particle size spray achieved | |

TABLE 3.2 aerosol compositions

| Example | 17 | 18 | 19 | 20 | 21 |
|---|---|---|---|---|---|
| Intended Form/Background/Detail | Aerosol/Spray concentrate | Aerosol/Spray concentrate | Aerosol/Spray concentrate | Aerosol/Spray concentrate | Aerosol/Spray concentrate |
| Methyl Palmitate | 5 | 3 | 7 | 4 | 3 |
| SDA40B Alcohol | 5 | 7 | 3 | 5.5 | 6 |
| Talc | 0 | 0 | 0 | 0.5 | 0 |
| Propylene glycol, USP | 0 | 0 | 0 | 0 | 1 |
| Batch Size (g) | 10 g | 10 g | 10 g | 10 g | 10 g |
| Processing Observations | Water clear solution | Water clear solution | Water clear solution | Cloudy mixture, talc settles easily | MEP + PPG-slightly cloudy, clear with alcohol |
| Stability-12 hr-Room temp | DNT | DNT | DNT | DNT | DNT |
| Stability-24 hr-Room temp | DNT | DNT | DNT | DNT | DNT |
| Freeze-Thaw-5 min-(−15° C.) | MEP freezes | MEP freezes | MEP freezes | MEP freezes | Solution freezes |

TABLE 3.3

Aerosol compositions

| Example | 22 | 23 | 24 | 25 | 26 |
|---|---|---|---|---|---|
| Intended Form/Background/Detail | Aerosol/Spray concentrate | Aerosol/Spray concentrate | Aerosol/Spray concentrate | Aerosol/Spray concentrate | AerosolSpray/concentrate |
| Methyl Palmitate | 5 | 3 | 7 | 4 | 3 |
| SDA40B Alcohol | 5 | 7 | 3 | 5.5 | 7 |
| Talc | 0 | 0 | 0 | 0.5 | 0 |
| Propylene glycol | 0 | 0 | 0 | 0 | 0 |
| Batch Size (g) | 10 g | 10 g | 10 g | 10 g | 10 g |
| Processing Observations | Water clear solution | Water clear solution | Water clear solution | Cloudy mixture, talc settles easily | Clear, colorless to to yellow liquid |
| Stability-12 hr-Room temp | DNT | DNT | DNT | DNT | Stable (12 hr) Stable (24 hr) |
| Freeze-Thaw-5 min-(−15° C.) | MEP freezes | MEP freezes | MEP freezes | MEP freezes | Solution freezes Sample sent to A&L. 6/26 Sample to Aptar 6/28 |

Aerosols prepared according to the foregoing were also tested in substantially the same manner as the deodorant/antiperspirant formulations described above and shown in Tables 2.1-2.3. The results of those tests are shown here:

TABLE 4 results of aerosol tests

| | EXAMPLE 15 | Comparative | EXAMPLE 16 | Comparative | Comparative |
|---|---|---|---|---|---|
| Lab Notebook Number | A1 | CA1 | A3 | CA1 | NT (No Treatment) |
| Product Form | Standard Aerosol | Antiperspirant stick | BOV Aerosol | Antiperspirant stick | NA |

TABLE 4-continued results of aerosol tests

|  | EXAMPLE 15 | Comparative | EXAMPLE 16 | Comparative | Comparative |
|---|---|---|---|---|---|
| Separation/Separation test | NA | NA | NA | NA | NA |
| Test subject details | 42 year old male, asian, history of mild hyperhidrosis | 42 year old male, asian, history of mild hyperhidrosis | 42 year old male, asian, history of mild hyperhidrosis | 42 year old male, asian, history of mild hyperhidrosis | 42 year old male, asian, history of mild hyperhidrosis |
| Application location | Left armpit | Right armpit | Left armpit | Right armpit | Right armpit |
| Application amount | 1 spray (approx. 0.5 seconds) | 2 swipes | 1 spray (approx. 0.5 seconds) | 2 swipes | NA |
| Ambient Conditions | Outdoors, 75° F., 50% RH, sunshine | Outdoors, 75° F., 50% RH, sunshine | Outdoors, 73° F., 40% RH, sunshine | Outdoors, 73° F., 40% RH, sunshine | Outdoors, 70° F., 50% RH, sunshine |
| Sweat Area (cm2) | 45 | 145 | 160 | 146 | 243 |
| Odor | Oily sweet | AP odor | No | AP odor | Body odor |
| Staining/transfer to clothing | No | No | No | No | NA |
| Skin irritation | No | No | No | No | NA |
| Application ease | Smooth-thin (transparent) | Smooth-thin | Smooth-thin (transparent) | Smooth-thin | NA |

As illustrated in Table 4, the standard aerosol application reduced the amount of sweat significantly without generating odor, skin irritation and staining.

As should be appreciated, compositions according to the disclosure are applied to the user and provide effective cooling relief. As the user's body temperature rises, the phase change material will melt, causing the user's skin to cool. The compositions described herein preferably are formulated to be retained on the user for an extended period of time, such that the user can repeatedly reap the cooling benefit. Preferably, the application is intended to stay on the user for up to 24 hours or until removed by the user. Other application modalities also are contemplated. For example, the compositions described above may be applied to a substrate that is adhered to the user's skin, as in a patch, tape or mask.

The inventor has further contemplated that these cooling formulations, either in spray aerosol, powder, body stick or any other form, could be formulated in conjunction with one or more functional additives. These functional additives may include perfumes, sunscreens (sun blocks), insect repellents, skin moisturizers, facial foundation powders or creams, shaving creams or gels, topical analgesic, antimicrobial agents, antifungals, antidandruff, hydrocortisone (or other anti-itch drugs), skin tanning oils or lotions, anti-chafing creams and soaps.

The invention has been described thus far as having a cooling effect on the wearer. This is not necessary. A phase change composition according to the invention could alternatively be formulated that is intended to warm the user. For example, a composition formulated according to the above-described embodiments and methods may include a reversible phase change material having a melting point at or below ambient temperature. Whenever the temperature drops below the melting point, the exothermic reaction accompanying the phase change from liquid to solid would give off heat, warming the wearer. Outdoor, cold-weather applications are an example of a contemplated use of such a warming composition.

While the invention has been described in connection with several presently preferred embodiments thereof, those skilled in the art will appreciate that many modifications and changes may be made therein without departing from the true spirit and scope of the invention which accordingly is intended to be defined solely by the appended claims.

The invention claimed is:

1. A topical composition comprising an epidermal coolant wherein said coolant comprises:
   (i) a phase change material that changes phase between 28° C. and 40° C., wherein the phase change material is methyl palmitate and comprises about 40% of the coolant;
   (ii) a solvent in which the phase change material is dissolved, wherein the solvent is hexamethyldisiloxane and comprises about 50% of the coolant; and
   (iii) a surfactant, wherein the surfactant contains cyclopentasiloxane, dimethiconol, and a silicone elastomer blend of cyclomethicone and dimethicone crosspolymer, and comprises about 10% of the coolant.

2. The topical composition of claim 1, further comprising a propellant.

3. The topical composition of claim 1, wherein the coolant is in an aerosol sprayer.

4. The topical composition of claim 1, further comprising a sunscreen compound as a functional additive.

5. The topical composition of claim 1, further comprising an insect repellent compound as a functional additive.

6. The topical composition of claim 1, wherein the solvent flashes off the skin when the coolant is applied to a user's epidermis.

7. The topical composition of claim 1, wherein the surfactant cooperates with the phase change material to make the material more soluble.

8. The topical composition of claim 1, wherein the surfactant forms a film on the user's epidermis to retain the phase change material on the epidermis, prevent absorption of the phase change material into the epidermis, or both.

9. The topical composition of claim 1, further comprising an antimicrobial agent as a functional additive.

10. A method of epidermal cooling comprising: applying the topical composition according to claim 1 to a user's epidermis, wherein the solvent flashes off or evaporates and leaves the phase change material in solid form; and melting the phase change material contained in the applied epidermal coolant when a temperature of the user's epidermis rises above the melting point of the phase change material, thereby resulting in an endothermic reaction that cools the user's epidermis.

11. The method of claim 10, wherein the topical composition is applied by a user via an aerosol sprayer.

12. The method of claim 10, wherein the topical composition is applied by a user via a bag-on-valve sprayer.

13. The method of claim 10, wherein the topical composition is applied by a user via a wet wipe.

14. An epidermal coolant comprising:
(i) a phase change material that changes phase between 28° C. and 40° C., wherein the phase change material is methyl palmitate and comprises about 40% of the coolant;
(ii) a solvent in which the phase change material is dissolved, wherein the solvent is hexamethyldisiloxane and comprises about 50% of the coolant; and
(iii) a surfactant, wherein the surfactant contains cyclopentasiloxane, dimethiconol, and a silicone elastomer blend of cyclomethicone and dimethicone crosspolymer, and comprises about 10% of the coolant.

15. The epidermal coolant of claim 14, wherein the solvent flashes off the skin when the coolant is applied to a user's epidermis.

16. The epidermal coolant of claim 14, wherein the surfactant cooperates with the phase change material to make the material more soluble.

17. The epidermal coolant of claim 14, wherein the surfactant forms a film on the user's epidermis to retain the phase change material on the epidermis, prevent absorption of the phase change material into the epidermis, or both.

18. A method of epidermal cooling comprising: applying the coolant composition according to claim 14 to a user's epidermis, wherein the solvent flashes off or evaporates and leaves the phase change material in solid form; and melting the phase change material contained in the applied epidermal coolant when a temperature of the user's epidermis rises above the melting point of the phase change material, thereby resulting in an endothermic reaction that cools the user's epidermis.

* * * * *